(12) United States Patent
Komatsu (10) Patent No.: US 8,965,724 B2
(45) Date of Patent: Feb. 24, 2015

(54) MEASURING DEVICE (75) Inventor: Yuichiro Komatsu, Kyoto (JP)

(73) Assignee: Horiba, Ltd. (JP)

( * ) Notice: Subject to any disclaimer, the term of this patent is extended or adjusted under 35 U.S.C. 154(b) by 529 days.

(21) Appl. No.: 13/412,047

(22) Filed: Mar. 5, 2012

(65) Prior Publication Data

US 2012/0226459 A1 Sep. 6, 2012

(30) Foreign Application Priority Data

Mar. 3, 2011 (JP) ................................. 2011-047008

(51) Int. Cl.
*G06F 19/00* (2011.01)
*G01N 27/416* (2006.01)

(52) U.S. Cl.
CPC .................................. *G01N 27/4163* (2013.01)
USPC .......................................................... 702/85

(58) Field of Classification Search
CPC ........ A61B 6/481; A61B 6/504; A61B 6/548; A61M 2205/3561
USPC ........................................... 702/85, 182–185
See application file for complete search history.

(56) References Cited

U.S. PATENT DOCUMENTS 6,735,535 B1 * 5/2004 Kagan et al. .................... 702/61
2009/0128124 A1 5/2009 Garland et al.

FOREIGN PATENT DOCUMENTS

| DE | 10141556 A1 | 3/2003 |
|---|---|---|
| JP | 04031786 A | 2/1992 |
| JP | 06308073 A | 11/1994 |
| JP | 8-220049 A | 8/1996 |
| JP | 2004-325077 A | 11/2004 |
| JP | 2009-244006 A | 10/2009 |

OTHER PUBLICATIONS

Summary of the Japanese Office Action dated Jun. 12, 2014, issued in JP Application No. 2011-047008, with English remarks.
Extended European Search Report for Application No. 12166127.6-2204, mailed Aug. 10, 2012, with English translation.
Keithley: "Model 2700 Multimeter/Switch System User's Manual", 2700-900-01 Rev. G, Aug. 2003, Cleveland, Ohio, USA, Retrieved from the Internet: URL:https://wikihost.uib.no/ift/images/4/4f/Keithley2700.pdf.
YSI: "Professional Plus User Manual", YSI—Homepage Item #605596, Rev. D, Drawing # A605596, Mar. 2009, Yellow Springs, OH, USA, Retrieved from the Internet: URL/http://www.ysi.com/media/pdfs/605596-YSI-ProPlus-User-Manual-RevD.pdf.

* cited by examiner

*Primary Examiner* — Edward Raymond
(74) *Attorney, Agent, or Firm* — Cantor Colburn LLP (57) ABSTRACT

The measuring device comprises a detection part provided with a pair of electrode parts to output a potential difference or a current value caused by contacting the respective electrode parts with a measurement object and a main body displaying, as a measurement result, a characteristic value of the measurement object obtained based on the potential difference, wherein the measuring device further comprises: a calibration start command receiving part receiving a calibration start command from a user; a stability degree calculation part calculating a degree of stability of the characteristic value based on a variation amount of the characteristic value; and a display output part displaying a value of the degree of stability itself at least before the calibration start command receiving part receives the calibration start command from the user.

4 Claims, 6 Drawing Sheets

MEASURING DEVICE

TECHNICAL FIELD

The present invention relates to a measuring device measuring a pH, oxidation/reduction potential, an ion concentration, a conductivity, and concentration of dissolved oxygen and the like of a measurement object.

BACKGROUND ART

Regarding a measuring device of this type, there is known one comprising a detection part that allows a pair of electrode parts to be brought into contact with a measurement object so as to generate a potential difference to be outputted and further comprising a main body displaying characteristic values pertaining to the pH, ion concentration and the like of the measurement object obtained based on the potential difference as the measurement results. For example, there is a proportional relationship between the potential difference and a logarithm of the ion concentration, and hence it becomes possible to perform an accurate measurement by previously executing a calibration using a reference solution of a known ion concentration before performing the measurement.

By the way, in the calibration performed in the device of this type, since the potential difference outputted from the electrode part is continuously varying for a while after immersing the electrode part into the reference solution, it is necessary to start the calibration after waiting until the variation amount becomes small to be stabilized. Since a timing of starting the calibration is differed according to differences in peripheral environment, concentrations of reference solutions and the like, an unskilled user may start the calibration without taking a sufficient wait time so that the accurate calibration cannot be done in some cases. In order to solve such a problem, there may be used a measuring device that automatically starts the calibration when it is determined by an internal calculation that the potential difference is stable within a tolerance range after a user immerses the electrode part into the reference solution.

In the measuring device having an automatic calibration function by the internal calculation mentioned above, as disclosed in Patent Literature 1, in such a case where the potential difference is not stabilized even after a predetermined time lapse, it is configured to output an error so as to stop the calibration. In other words, if the measuring device having such an automatic calibration function is used, even though the electrode part is immersed into the reference solution the calibration is not always finished but there may result in causing a case, even being rare, where an error is generated so as to stop the calibration.

If a stop of the calibration occurs, since the stability of the potential difference is merely determined by the internal calculation in the measuring device, the user cannot determine as to whether the reference solution is actually unstable or there is a problem in the measuring device itself. If there arises such a doubt, even when the calibration is successful without a problem in the measuring device, the user is apt to consider that a problem may actually arise in the measuring device thereby damaging the reliability of the measuring device.

Figure 6:
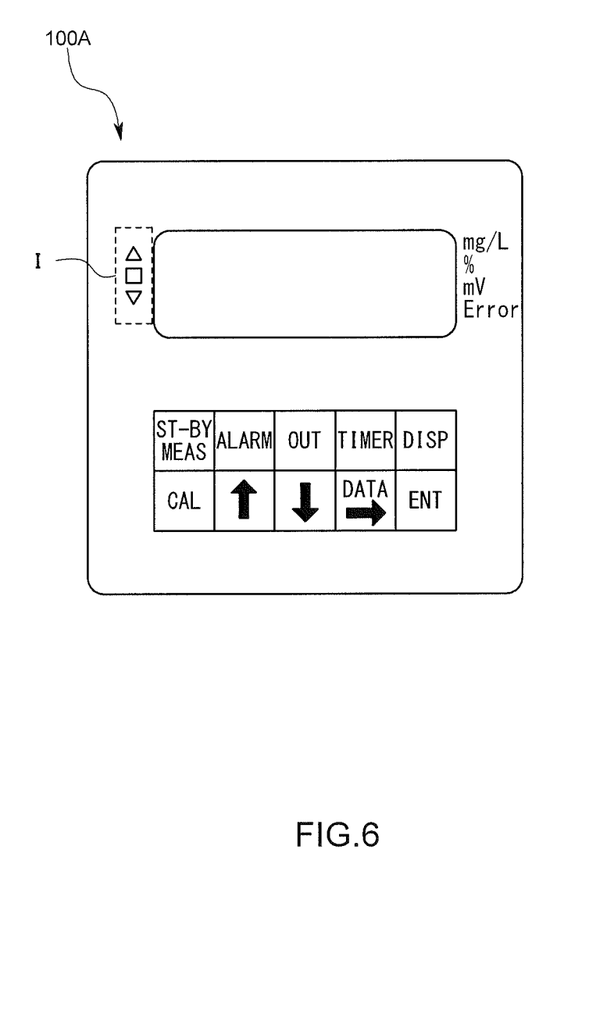
FIG. 6 is a conventional measuring device having a function of informing a user of a degree of stability of a reference solution by a flashing period of an indicator.

Meanwhile, as shown in Patent Literature 2 and FIG. 6, in the case of an ion concentration measuring device 100A in which a calibration is performed by a manual operation and stability or instability of a potential difference is informed by a flashing period of an indicator I, it may appear that the problem concerning the reliability as mentioned above can be even solved.

However, even in the measuring device 100A shown in Patent Literature 2, since the flashing period is merely varied, the user cannot understand merely by watching the indicator I or a display screen and the like as to why the measuring device determines that the potential difference is stable. Therefore, there is a first problem that, if an error occurs after starting a calibration so that the calibration is forcibly stopped similarly to the conventional one, the reliability of the indicator I and the measuring device 100A is still lost.

Further, in the measuring device 100A shown in Patent Literature 2, there is a problem also in a measure of a degree of stability used in the internal calculation, in ensuring the reliability of the calibration. Specifically, in this measuring device, the degree of stability $\Delta$ as to whether the potential difference is stable is determined by an assessment as to whether a value obtained by dividing a difference between a current potential difference En and a potential difference Em before a predetermined time by a electrode sensibility S ranges within a predetermined fixed threshold. Moreover, since it is known that the potential difference and a logarithm of the ion concentration is proportional, when using concentrations Cn and Cm together with constants Gl and Gu indicative of the lower limit and upper limit of the thresholds corresponding to En and Em and assuming that an equation (Cn=Cm+a) can be described using a variation range "a", this results in that the determination of the stability is performed in the measuring device under the condition as following.

$$G_l < \Delta = \frac{En - Em}{S} \qquad \text{[Equation 1]}$$
$$= \log_{10} \frac{Cn}{Cm}$$
$$= \log_{10}\left(1 + \frac{a}{Cm}\right) < G_u$$

In other words, it is concluded that the stability is evaluated by a logarithm of a ratio of the ion concentrations indicative of the characteristic values. Herein, assuming that the variation range "a" can be represented as a substantially a constant value obtained by Equation 1 irrespective of the concentration, since the degree of stability $\Delta$ is a logarithm value of the concentration, the lower the concentration of Cm, the larger the degree of stability $\Delta$ becomes, and conversely the higher the concentration of Cm, the degree of stability $\Delta$ is outputted as the smaller value. Therefore, since the threshold is fixed as shown in Equation 1, even if the variation range "a" is substantially equal in the respective ion concentrations during execution of the calibration, it becomes that the stability is determined with a tight criterion in the case of using a reference solution of a low concentration. Conversely, in the case of using a reference solution of a high concentration, it becomes that the stability is determined with a mild criterion.

As described above, in the measuring device of Patent Literature 2, there is a second problem that, if a calibration is performed using reference solutions having a plurality of different characteristic values, the determination criterion of the degree of stability has been varied so that the reliability of the calibration cannot be sufficiently ensured.

CITATION LIST

Patent Literature

Patent Literature 1: JP H08-220049A
Patent Literature 2: JP2009-244006A

SUMMARY OF INVENTION

Technical Problem

The present invention has been made in consideration of the respective problems as described above, and an essential object of the present invention is to provide a measuring device that allows a user to start a calibration after having confidence that the state becomes suitable for performing the calibration irrespective of a characteristic value of a reference solution so that a calibration result thereof can be obtained with high reliability.

Solution to Problem

That is, a measuring device of the present invention comprises a detection part provided with a pair of electrode parts to output a potential difference caused by contacting the respective electrode parts with a measurement object and a main body displaying, as a measurement result, a characteristic value of the measurement object obtained based on the potential difference, wherein the measuring device further comprises: a calibration start command receiving part receiving a calibration start command from a user; a stability degree calculation part calculating a degree of stability of the characteristic value based on a variation amount of the characteristic value; and a display output part displaying a value of the degree of stability itself at least before the calibration start command receiving part receives the calibration start command from the user.

With this configuration, since the display output part displays on the main body the value of the degree of stability itself calculated based on the variation amount of the characteristic value before the user inputs the calibration start command, the user can input the calibration start command after confirming that the value of the degree of stability becomes stable. That is, the measuring device does not arbitrarily start the calibration based on such as a threshold previously set in the measuring device but the user can start the calibration after the user is convinced of the degree of stability, and therefore it becomes possible for the user to rely on the calibration result thereof. Even if a calibration is failed due to some error after inputting the calibration start command, since the user himself confirms the degree of stability, the user can be convinced that there is no problem in a side of the measuring device but there is an error in determination of the degree of stability by the user so that loss of the reliability on the measuring device can be prevented.

Moreover, since the degree of stability is calculated from the variation amount of the characteristic value obtained based on the potential difference, the sensibility to the variation amount is differed depending on the characteristic value so that an erroneous evaluation of the degree of stability can be prevented. In other words, since the degree of stability is calculated from the variation amount of the characteristic value, even if the reference solution for use in the calibration is different, the variation amount appears as a change of the degree of stability by the same amount so long as the variation amount is the same, and hence the stability can be determined based on a uniform criterion without a deviation.

Thus, the reliability on the calibration result of the measuring device and the measurement result based thereon by the user can be further increased.

In order to facilitate the user to determine whether the state is suitable for starting the calibration based on the degree of stability, it is preferable that the stability degree calculation part calculates the degree of stability every predetermined period and the degree of stability may be a difference between a maximum and a minimum of the characteristic value obtained in the predetermined period. With this configuration, since the degree of stability is displayed every predetermined period, the user can grasp a tendency of the degree of stability more easily compared to a case of the value being frequently varied by a fine noise and the like.

In order to prevent that the user doubts that the criterion and the like of calculating the degree of stability is changed for every characteristic value so that the reliability on the calibration is lost, the display output part is preferably configured to display the present characteristic value itself together with the degree of stability.

Advantageous Effects of Invention

Thus, according to the present invention, since the display output part displays the degree of stability calculated from the variation amount of the characteristic value before the user inputs the calibration start command, the user can start the calibration after the user is convinced as to whether or not the value of the degree of stability becomes stable. Therefore, in the conventional measuring device, the calibration is started and ended in a manner of managing by a black box so that the user's reliability on the measuring device is lost when an error and the like occurs, whereas in the present invention, since the user is convinced of the degree of stability, it is possible to prevent the reliability on the calibration result and the measuring device from being doubted. In addition, since the degree of stability is calculated from the variation amount of the characteristic value, the degree of stability can be evaluated by a constant criterion all the time irrespective of a scale of the characteristic value so that the reliability on the calibration result and the measuring device can be further improved.

REFERENCE SIGNS LIST

100 . . . Measuring device
1 . . . Main body
2 . . . Electrode part

Figure 1:
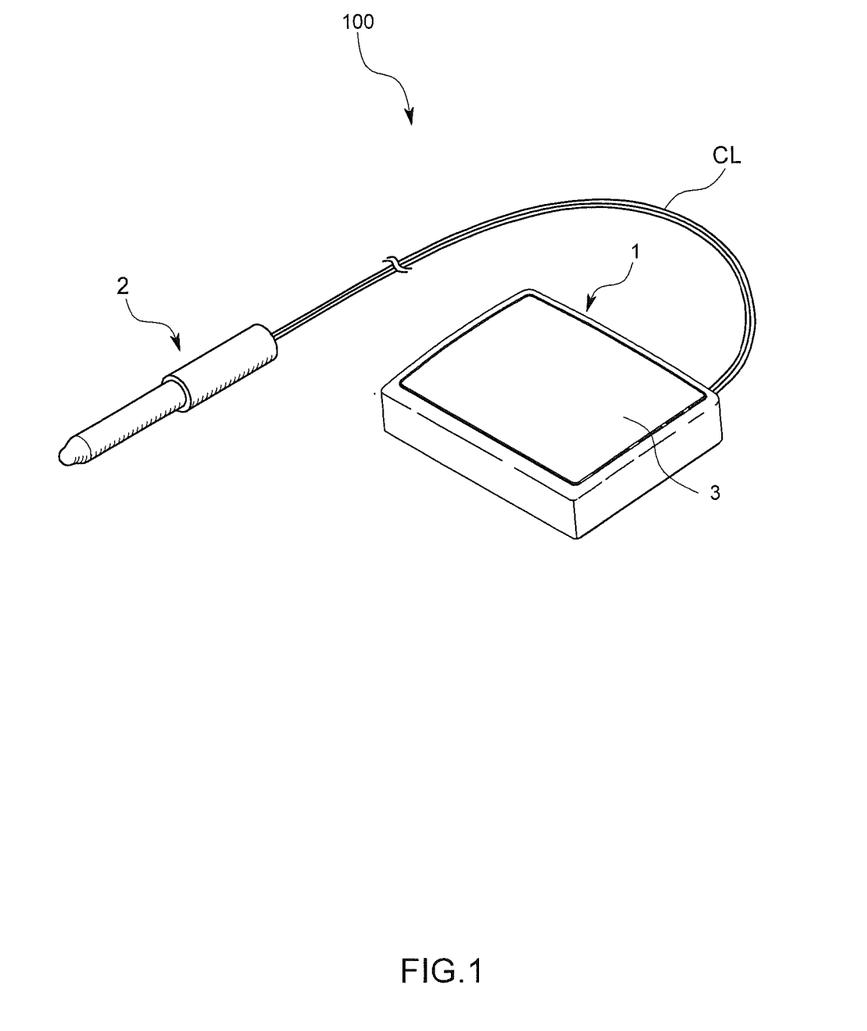
FIG. 1 is a schematic perspective view showing a measuring device in one embodiment of the present invention.

21 ... Detection part
6 ... Calibration start command receiving part
7 ... Stability degree calculation part
8 ... Display output part Description Of Embodiments The following describes one embodiment of the present invention with reference to the drawings. As shown in FIG. 1, a measuring device 100 of the present embodiment comprises a probe 2 to be brought into contact with a measurement object and a main body 1 connected to the probe 2 via wireless or a wired cable CL and measures a pH, oxidation/reduction potential, ion concentration, conductivity and dissolved oxygen to display the measured values thereof on a touch-panel type display 3 provided on the main body 1. Then, the measuring device is configured to be able to switch an operation mode between a measuring mode for measuring each of characteristic values of a measurement object and a calibration mode for performing a calibration based on a reference solution having each of the known characteristic values.

Referring to each part in detail, as the probe 2, a plurality of types, i.e., an ion concentration measuring probe, a pH measuring probe, an oxidation/reduction potential measuring probe, a conductivity measuring probe and a dissolved oxygen measuring probe are prepared according to a measurement object so that the probe 2 appropriate for the measurement object is connected to the main body 1 so as to be used. In the present embodiment, the following description is made using the ion concentration measuring probe as a representative example of the probe 2.

The ion concentration measuring probe is so-called a composite electrode integrally provided with an ion concentration measuring electrode and a reference electrode and sensing portions of the ion concentration measuring electrode and reference electrode are exposed at a tip end thereof so as to be brought into contact with a measurement object such as an aqueous solution. A potential difference generated between the ion concentration measuring electrode and the reference electrode is rendered to be outputted as a probe signal. It is noted that, although a standard glass electrode type is shown in FIG. 1, it is not limited to this and, for example, a needle type one having a sharp-pointed tip may be also used, and further it is needless to say that various types of the probe having such as a configuration of separately providing the ion concentration measuring electrode and the reference electrode may be also used.

Figure 2:
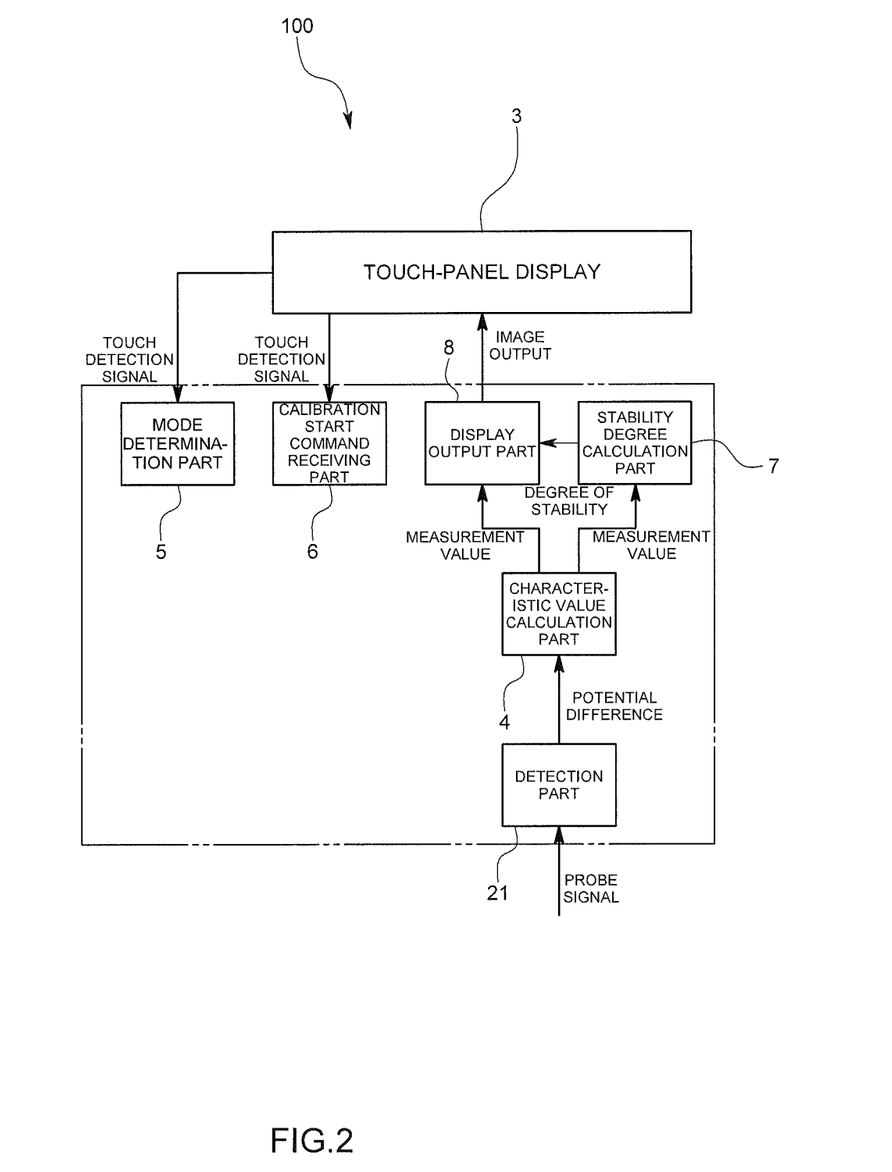
FIG. 2 is a functional block diagram of the measuring device in the same embodiment.

The main body 1 is provided with a CPU, an A/D converter, a memory, a touch-panel type display 3 comprising input/output means integral with a display, and the like as a hardware configuration. Herein, the CPU and the peripherals thereof, as needed, are operated based on programs stored in the memory so that the main body 1 is configured to function as at least a detecting part 21, a characteristic value calculation part 4, a mode determination part 5, a calibration start command receiving part 6, a stability degree calculation part 7 and a display output part 8 as shown in the function bloc diagram of FIG. 2.

Each of the parts is described below.

The detection part 21 is configured to output a value of the potential difference generated between the respective electrodes based on the probe signal from the probe 2. For example, an A/D converter and a sampler and the like correspond to the detection part 21.

The characteristic value calculation part 4 switches a transformation formula and calibration data respectively for use in accordance with the types of the probe 2 connected to the main body so as to calculate any of the ion concentration value, pH value, oxidation/reduction potential, conductivity and dissolved oxygen serving as the characteristic values of the measurement object. In the present embodiment, the ion concentration value is outputted based on the potential difference measured by the probe 2. More specifically, the characteristic value calculation part 4 calculates the ion concentration of the characteristic value by substituting the potential difference into a predetermined computing equation such as, e.g., Nernst Equation. In addition, the characteristic value calculation part 4 is configured to always calculate a new ion concentration value from a potential difference obtained every predetermined sampling period. Note that, as a method of calculating a characteristic value based on a potential difference, there are various available methods such as obtaining a characteristic value from a potential difference with reference to a previously created table indicating a relationship between the potential difference and the characteristic value.

Figure 3:
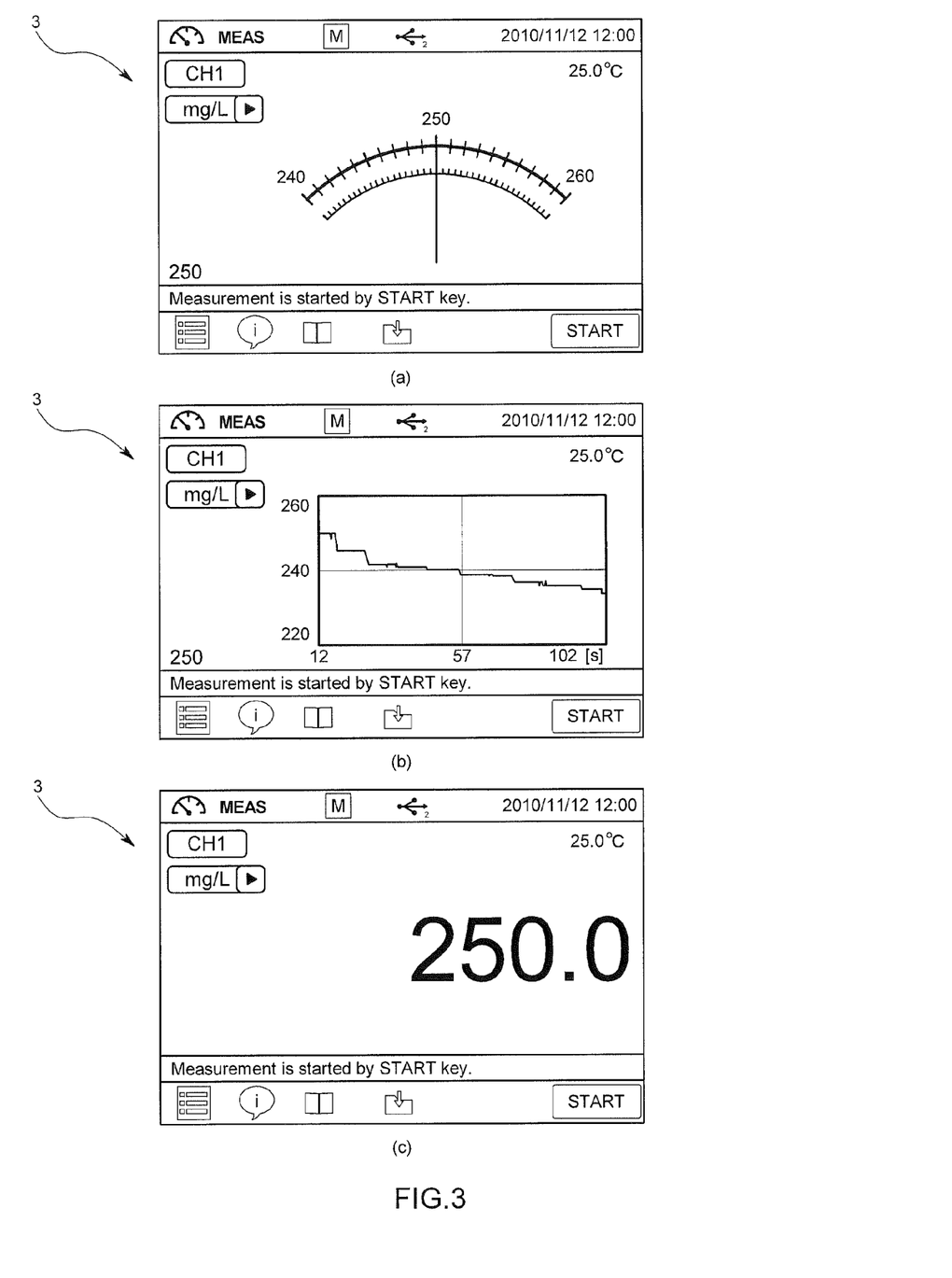
FIG. 3 is a diagram showing an example of a screen display in a measuring mode displayed on the measuring device in the same embodiment.
Figure 4:
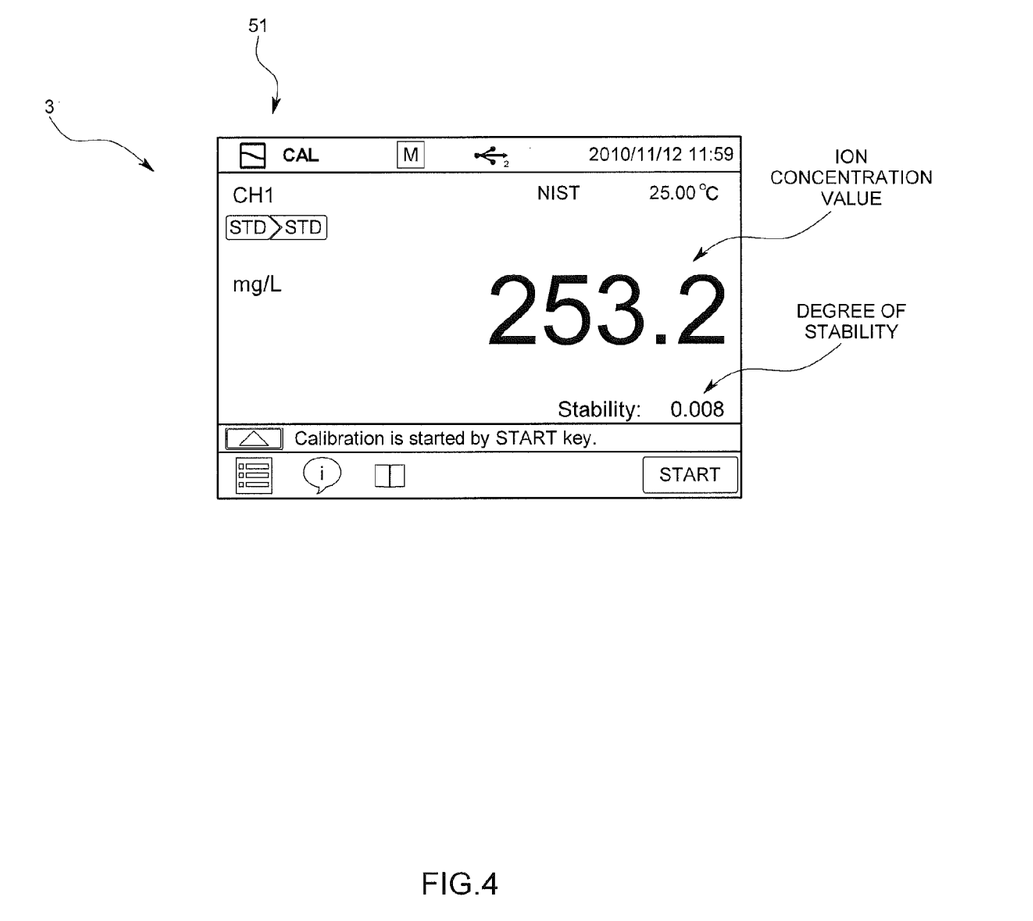
FIG. 4 is a diagram showing an example of a screen display in a calibration mode displayed on the measuring device in the same embodiment.

The mode determination part 5 determines in which mode the measuring device 100 is operated between the measuring mode (MEAS mode) for measuring an ion concentration value of a measurement object and the calibration mode (CAL mode) for calibrating the reference solution. More specifically, it is configured for a user to select any one of the modes for operating the measuring device through a mode selection part 51 located at an upper left portion on the touch-panel. When the measuring mode is selected, the display output part 8 to be described later displays the ion concentration values calculated by the characteristic value calculation part 4 as the respective measurement values as shown in FIG. 3. Herein, the respective drawings shown in FIG. 3 are switched to each other to be displayed as separated pages, and when a user inputs a touch-slide operation in a right and left direction with respect to the touch-panel type display 3, a display format of the page is switched to another one. That is, the display page is switched from an analog instrument display page shown in FIG. 3 (a) to a time series display page shown in FIG. 3 (b) or a numeric display page shown in FIG. 3 (c) and the like in accordance with necessity. When the calibration mode is selected, the display page is switched to a calibration page as shown in FIG. 4.

In this calibration page, there are displayed at least an ion concentration value calculated by the characteristic value calculation part 4 based on a potential difference outputted from the probe 2, a degree of stability to be described later and a start button to be inputted by a user for starting the calibration.

The calibration start command receiving part 6 receives a calibration start command from a user and corresponds to the start button displayed in the above calibration page in the present embodiment. The calibration is not started until the user touches the start button, and when the start button is touched, the calibration is performed based on a relationship between the potential difference and the characteristic value at that time or after subjecting to a predetermined number of samplings from that time. Thus, in the present embodiment, the calibration is not performed only by immersing the probe into the reference solution by the user, and the calibration is started only after the user has inputted the calibration start command through the start button.

The stability degree calculation part 7 calculates the degree of stability of the corresponding characteristic value based on the variation amount of the ion concentration value which is the characteristic value. That is, in the present embodiment, the degree of stability is not calculated from the potential difference but the degree of stability is calculated using the ion concentration value itself transformed by a predetermined computing equation from the potential difference. For example, the stability degree calculation part 7 calculates the degree of stability by substituting the variation amount of the characteristic value into a predetermined computing equation, or calculates the degree of stability by an arithmetical operation using the variation amount value itself of the characteristic value. Referring to the calculating method of the degree of stability more specifically, the stability degree calculation part 7 calculates the degree of stability every predetermined period, so that the difference between a maximum value and a minimum value of the characteristic value obtained in the predetermined period is used as the degree of stability. In other words, whereas the ion concentration value which is the characteristic value is renewed every sampling period, the degree of stability is outputted only one time after a plurality of samplings are executed, and therefore the frequency of renewal is lowered compared to that of the ion concentration value. A specific equation of the degree of stability can be described as below.

$$\Delta = f(E(t_{max})) - f(E(t_{min}))$$ [Equation 2]

Herein, $\Delta$: degree of stability, $f(\ )$: function for transforming a potential difference to a characteristic value, $E(t)$: potential difference at a certain time $t$, $t_{max}$: a time when the characteristic value becomes maximum in the predetermined period, and $t_{min}$: a time when the characteristic value becomes minimum in the predetermined period.

Figure 5:
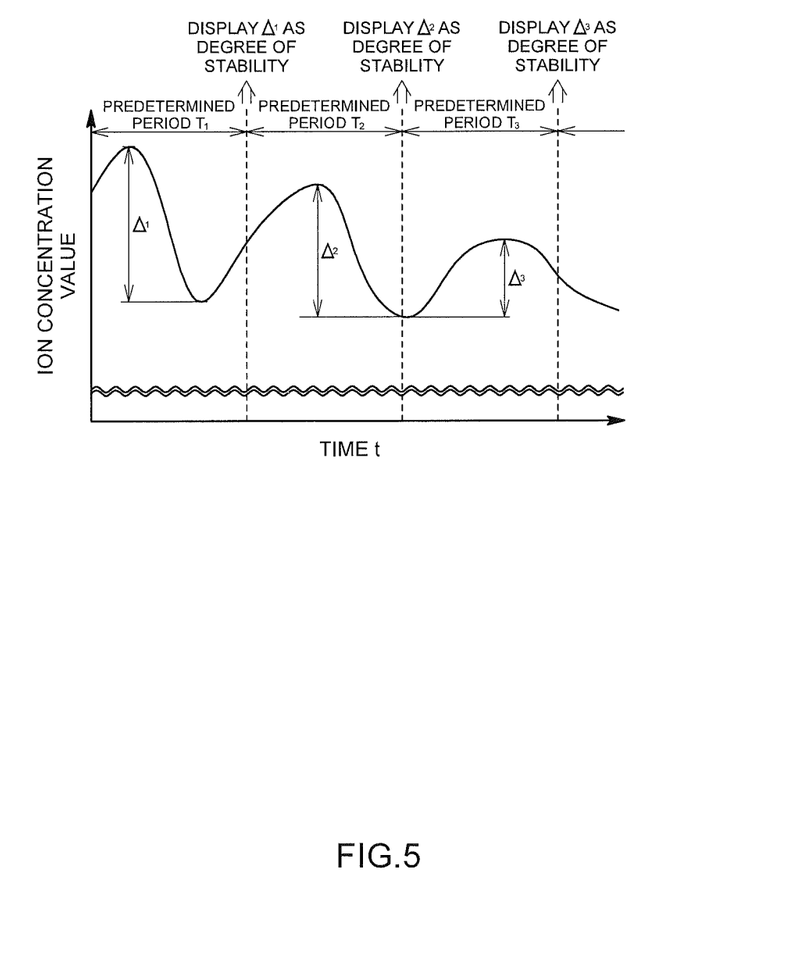
FIG. 5 is a graph conceptually showing a calculating method of a degree of stability in a stability degree calculation part in the same embodiment.

Assuming that each predetermined period is $T_n$, and the degree of stability corresponding to each predetermined period is $\Delta n$, a concrete example of the calculated degree of stability in the stability degree calculation part 7 configured as described above is outputted as shown in FIG. 5, and thus the display of the degree of stability in the display screen shown in FIG. 4 is to be renewed.

The display output part 8 is configured to display the ion concentration value measured at the present time on the screen in the measuring mode and display the stability degree value itself before at lest the calibration start command receiving part 6 receives the calibration start command from the user in the calibration mode. More specifically, as shown in FIG. 4, the display output part 8 is configured to display the ion concentration value indicative of the characteristic value at a central portion of the screen and also displays a numeric value of the degree of stability by an inscription smaller than the ion concentration value. Also, a display urging the user to execute the calibration is performed at least until the user inputs the calibration start command through the start button. Further, the ion concentration value and the degree of stability are displayed with their numbers of digits made equal.

According to the measuring device 100 of the present embodiment configured as described above, in the calibration page displayed in the case of selecting the calibration mode, since the numeric value itself of the degree of stability is displayed at least until the user inputs the calibration start command, the user can easily confirm whether the state is suitable for performing the calibration when the probe is immersed into the reference solution. And yet, since the numeric value itself of the degree of stability is displayed, the outputted degree of stability can be easily convinced without giving the user an insecure feeling that the user cannot know what is internally being executed in the measuring device 100. Therefore, the calibration can be started while the user himself is convinced, even if an error and the like is outputted after starting the calibration, it is possible to prevent the thought that there is a problem in a side of the measuring device 100. As a result, the calibration results and measurement results that have ever been performed can be made reliable by the user.

In addition, since the degree of stability is calculated from the variation amount of the ion concentration value itself which is the characteristic value transformed from the potential difference, even if the order of the ion concentration value is different, it can be similarly calculated as the degree of stability so long as the variation is in the same range. In other words, since the calculating method of the degree of stability is set so that a linearity between the degree of stability and the variation amount of the characteristic value can be held overall the characteristic values, the evaluation of the degree of stability can be uniformly performed irrespective of the order. Therefore, the degree of stability can be seen with the same criterion even in the reference solution having a different ion concentration value, and hence the user's reliability on the calibration result can be more improved.

Other embodiments are described below.

In the embodiment described above, although the explanation is made based on the ion concentration value, even if the other characteristic values are used, it may be configured similarly. That is, the degree of stability may be also calculated based on a difference of a pH value transformed from the potential difference or a difference and the like of such as a conductivity transformed from the current value. Further, in the embodiment described above, although the numeric value itself of the degree of stability is displayed before the calibration start command is inputted, it may be also possible to display a time series graph and the like indicative of the stability degree value itself. In addition, the calculating method of the degree of stability is not limited to only taking a difference of the characteristic value. For example, it may be configured to calculate the degree of stability based on a differentiation of the characteristic value. Briefly speaking, it is sufficient that the degree of stability is calculated from a value related to the variation amount of the characteristic value.

In addition, the present invention is not limited to the embodiments described above, and various modifications and combination of the embodiments may be made within a range without departing from the spirit of the invention.

Industrial Applicability

According to the measuring device of the present invention, since the display output part displays the degree of stability calculated from the variation amount of the characteristic value before the user inputs the calibration start command, the user can start the calibration after the user is convinced as to whether or not the value of the degree of stability becomes stable. Therefore, in the conventional measuring device, the calibration is started and ended in a manner of managing by a black box so that the user's reliability on the measuring device is lost when an error and the like occurs, whereas in the present invention, since the user is convinced of the degree of stability, it is possible to prevent the reliability on the calibration result and the measuring device from being doubted. In addition, since the degree of stability is calculated from the variation amount of the characteristic value, the degree of stability can be evaluated by a constant criterion all the time irrespective of a scale of the characteristic value so that the reliability on the calibration result and the measuring device can be further improved.

The invention claimed is:

1. A measuring device comprising a detection part provided with a pair of electrode parts to output a potential difference caused by contacting the respective electrode parts with a measurement object and a main body displaying, as a measurement result, a characteristic value of the measurement object obtained based on the potential difference, wherein the measuring device further comprises: a calibration start command receiving part receiving a calibration start command from a user;

a stability degree calculation part calculating a degree of stability of the characteristic value based on a variation amount of the characteristic value; and a display output part displaying a value of the degree of stability itself at least before the calibration start command receiving part receives the calibration start command from the user.

2. The measuring device according to claim 1, wherein the stability degree calculation part calculates the degree of stability every predetermined period and the degree of stability is a difference between a maximum and a minimum of the characteristic value obtained in the predetermined period.

3. The measuring device according to claim 1, wherein the display output part is configured to display a present characteristic value itself together with the degree of stability.

4. A measuring device comprising a main body displaying, as a measurement result, a characteristic value of a measurement object obtained based on a signal caused by contacting a pair of electrode parts with the measurement object, wherein the measuring device further comprises: a calibration start command receiving part receiving a calibration start command from a user;

a stability degree calculation part calculating a degree of stability of the characteristic value based on a variation amount of the characteristic value; and a display output part displaying a value of the degree of stability itself at least before the calibration start command receiving part receives the calibration start command from the user.

* * * * *